United States Patent [19]

Smith et al.

[11] Patent Number: 5,482,032
[45] Date of Patent: Jan. 9, 1996

[54] DRY POWDER INHALERS

[75] Inventors: David K. Smith, Loughborough; Peter D. Hodson, Trowell; Anthony C. L. Wass, Stamford, all of England

[73] Assignee: Astra Aktiebolag, Sodertalje, Sweden

[21] Appl. No.: 273,898

[22] Filed: Jul. 12, 1994

[30] Foreign Application Priority Data

Jul. 14, 1993 [GB] United Kingdom ............... 9314614

[51] Int. Cl.$^6$ .................................. A61M 15/00
[52] U.S. Cl. .................... 128/203.15; 604/58
[58] Field of Search ............... 128/203.15, 203.19, 128/203.21, 203.23, 203.24; 604/58

[56] References Cited

U.S. PATENT DOCUMENTS 3,059,815  10/1962  Parsons ......................... 604/58
5,160,016  11/1992  Moksnes ........................ 198/533

FOREIGN PATENT DOCUMENTS

| 0469814 | 2/1992 | European Pat. Off. | 128/203.15 |
| 2516387 | 11/1981 | France | 128/203.15 |
| 644790 | 12/1993 | Switzerland | 604/58 |
| WO90/13327 | 11/1990 | WIPO | A61M 15/00 |
| WO90/13328 | 11/1990 | WIPO | A61M 15/00 |
| 9205824 | 4/1992 | WIPO | 128/203.15 |
| 9208509 | 5/1992 | WIPO | 128/203.12 |

Primary Examiner—Edgar S. Burr
Assistant Examiner—William J. Deane, Jr.
Attorney, Agent, or Firm—Fish & Richardson

[57] ABSTRACT

The present invention relates to a device for dislodging powder carried on the surface of a flexible sheet material. The device incorporates a resettable impactor including a head for striking the sheet material, wherein the head comprises an elongate striking surface which is curved in both planes orthoganol to the plan of the sheet material.

25 Claims, 3 Drawing Sheets

DRY POWDER INHALERS

BACKGROUND OF THE INVENTION

This invention relates to dry powder inhalers and in particular to dry powder inhalers in which powdered medicament is carried on the surface of a flexible sheet material prior to dispensing.

Asthma and other respiratory diseases have long been treated by the inhalation of appropriate medicament. For many years the two most widely used and convenient choices of treatment have been inhalation of medicament from a drug solution or suspension in a metered dose inhaler (MDI), or inhalation of powdered drug and perhaps excipients from a dry powder inhaler (DPI). With growing concern being voiced over the damage done to the earth's ozone layer by CFC's (chlorofluorocarbons) which are in widespread use in existing MDI'S, heightened interest in DPI systems has been stimulated.

W090/13328 discloses a dry powder inhalation device comprising a housing defining a chamber in communication with a patient port in the form of a mouthpiece or nasal adaptor, and an elongate carrier bearing a powdered medicament, the device being constructed and arranged such that areas of predetermined size of the elongate carrier may sequentially be exposed within the chamber, the device comprising one or more air inlets such that when a patient inhales through the patient port an air flow is established from the air inlet(s) to the patient port through the chamber such that particles of the powdered medicament of respirable size from said exposed area of the elongate carrier are entrained within the air flow.

SUMMARY OF THE INVENTION

In one aspect, the invention features a device for delivering a powder, including a flexible sheet material carrying a powder to be delivered on a surface thereof, and an improved impactor for dislodging the powder from the sheet material. The improved impactor includes a shaft having a first end that is mounted within the device, and a cantilevered arm extending from the shaft to a second, free end that is moveable between a first, primed position and a second position, towards which it is biased, in which at least a portion of the arm impacts a substantially planar portion of the flexible material. The movement of the shaft between the first and second positions defines a plane of motion, and at least a portion of the cantilevered arm, disposed intermediate (i) the intersection of the arm with the shaft and (ii) the free end, extends out of a first plane that includes the shaft and is perpendicular to the plane of motion of the shaft, towards a second plane that is defined by the substantially planar portion of the sheet.

The device generally comprises means to advance the elongate carrier to expose an area of said carrier within the chamber, said means being operable prior to or during patient inhalation through the patient port and means for releasing medicament of respirable size from the exposed area of carrier, e.g. in the form of means for impacting or striking the exposed area of the carrier either singularly or by a plurality of such strikings or impactions.

W092/08509 discloses a breath-actuated triggering mechanism which is suitable for use in such a device and GB Patent Application No. 9123953 discloses a deagglomerator suitable for use with dry powder inhalers.

EP-455463 discloses the use of microdimpled materials to hold doses of powdered medicament for inhalation therapy. Such materials may be in the form of an elongate substrate in which a surface of the substrate comprises:

(i) one or more grooves of width 10 to 500 μm at the carrier surface and depth 10 to 500 μm, the grooves containing particles of powdered medicament, (ii) randomly orientated pores of diameter 0.1 to 100 μm, at least a portion of the pores being on the exterior surface and containing particles of powdered medicament, (iii) apertures of diameter 1 to 100 μm in at least one surface produced by laser drilling, the apertures containing particles of powdered medicament, or, (iv) an embossed surface.

It has been found that the particular form of an impactor for dislodging powdered medicament from a carrier can significantly affect the amount of medicament dislodged and hence the performance level of the dry powder inhaler.

According to the present invention there is provided a device with an impactor for dislodging powder carried on the surface of a flexible sheet material, the device comprising means to support a substantially planar portion of the sheet material and a resettable impactor comprising a head for striking said portion of the sheet material and means to propel the head from a primed position distant from said portion of the sheet material to strike said portion of the sheet material characterized in that the head comprises an elongate striking surface which is curved in both planes orthogonal to the plane of said planar portion of the sheet material.

The impactor of the present invention has a form designed to provide uniform impactions to provide consistent and effective release of powder from the sheet material. The form of the impactor is also designed to provide uniform resetting and triggering release actions. It is also designed to be as independent as possible of manufacturing tolerances, e.g. by appropriate selection of the shape of tail, by having at least two turns in the spring region, by curvature of the head, etc.

The curved shape of the head, in particular, confers several advantages, referred to below. Experimental results have shown that the need for such a curved, springy head is crucial if shock waves in the tape to produce adequate powder release are to be obtained. Use of pressed steel impactor heads on plastic impactor bodies, or even of short metal spring wire heads rigidly attached at the elbow to a rigid impactor body, both gave rise to much reduced drug release, demonstrating the need for a springy, undamped impactor arm and head.

The impactor is preferably in the form of a single component and comprises an integral spring to store energy for impaction, together with a curved head region for striking the powder bearing tape. The nature of the impactor is important, as it must be sufficiently springy to be able to elastically store energy and to transmit that energy efficiently via the head region to the sheet material. A preferred form of the impactor is bent from a length of steel spring wire. The curved shape of the head region is particularly critical.

The impactor of the invention is useful in dry powder inhalers, particularly inhalers disclosed in W090/13328, W092/08509 and GB9123953.

BRIEF DESCRIPTION OF THE DRAWINGS

The invention will now be described with reference to the accompanying drawings in which.

DETAILED DESCRIPTION OF PREFERRED EMBODIMENTS

Figure 1:
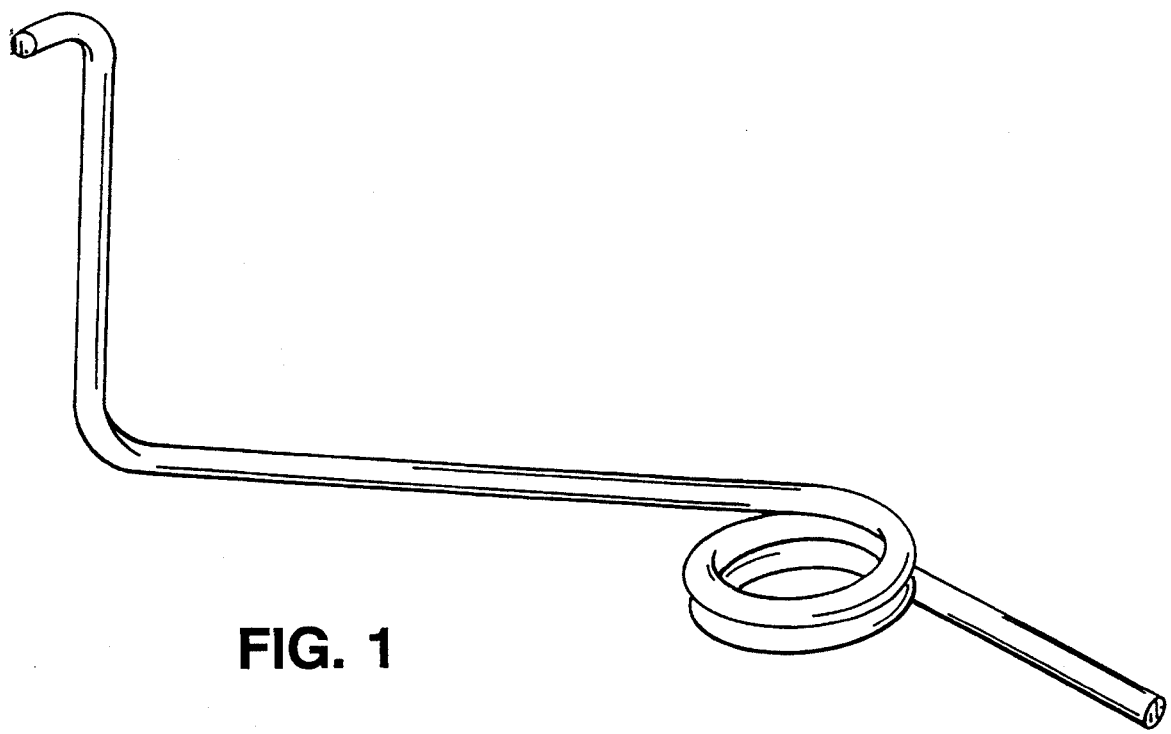
FIG. 1 is a perspective view of an impactor according to one embodiment of the invention.
Figure 1A:
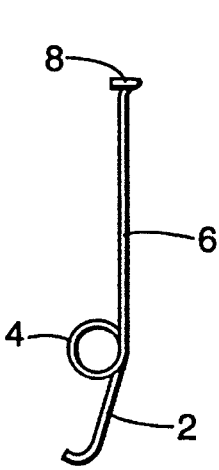
FIGS. 1(a) to (c) represent plan, side and end views of an impactor as shown in FIG. 1.
Figure 1B:
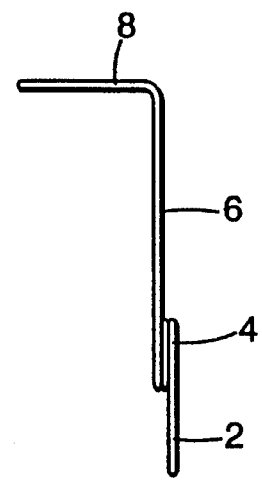
Figure 1C:
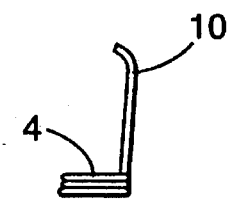

The impactor shown in FIG. 1 is a single component formed from spring steel. It has four main regions, the tail (2), the spring (4), the shaft (6) and the cantilevered arm (8). For an exemplary total length of ~96 mm, the different regions may comprise ~14, 38, 29, 15 mm respectively.

Figure 2:
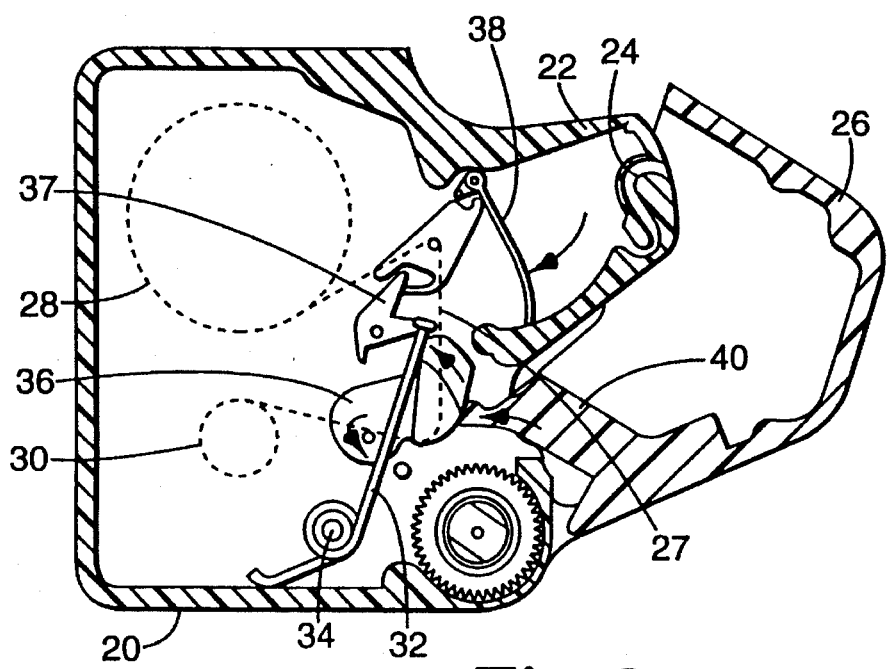
FIG. 2 represents a diagram of a breath-actuated dry powder inhaler in accordance with the invention.
Figure 3:
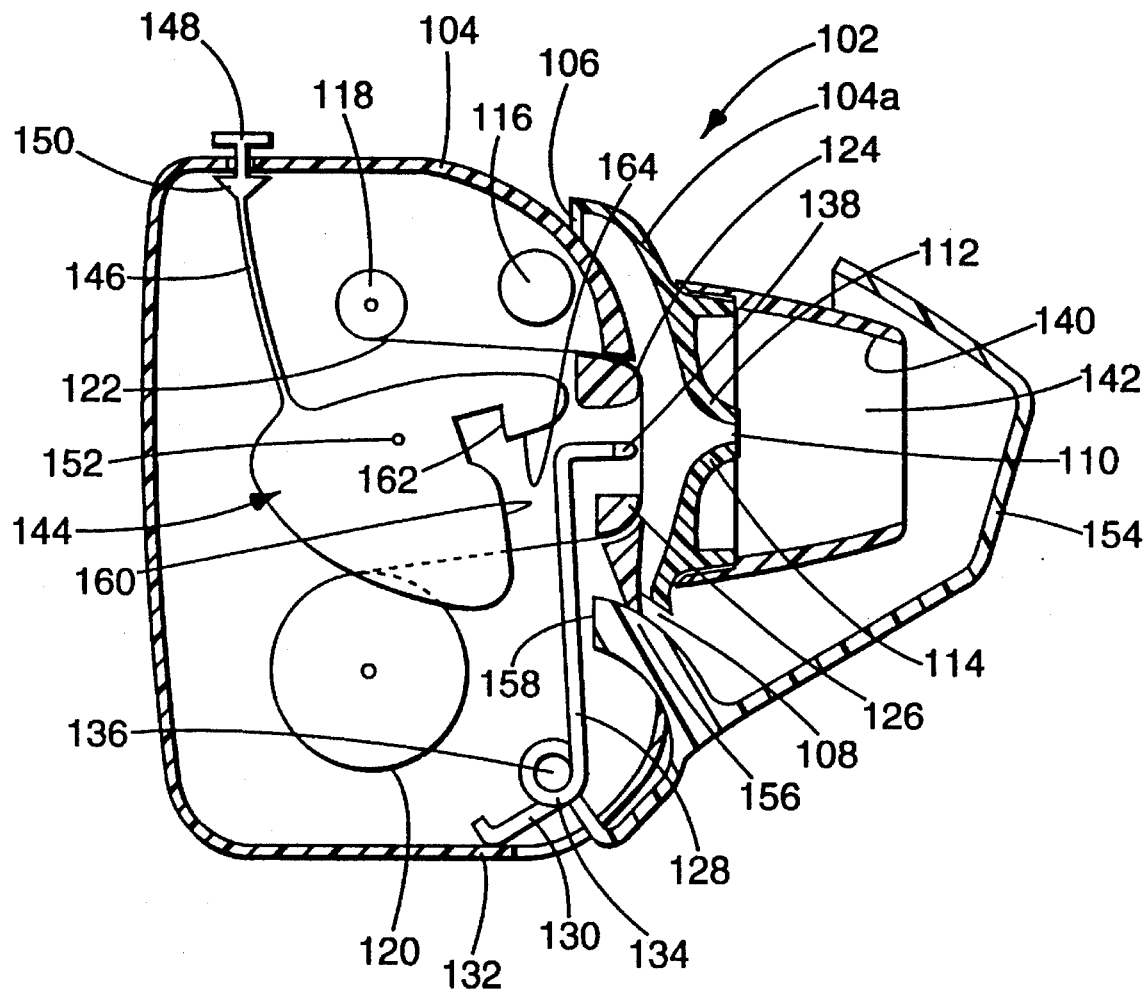
FIG. 3 represents a diagram of a manually operated dry powder inhaler.

The function of the tail region (2) is to provide anchorage of the end of the spring region (4) against rotation during resetting of the impaction mechanism (storage of energy in the impactor by torsion of the coils of the spring). As such the tail (2) is designed to bear on the outer wall of the device body during resetting (FIGS. 2 and 3). The tail (2) or other fixed portion may be curved to prevent it from damaging this plastic wall or from "digging in" and thus altering the setting point, etc.

The function of the spring region (4) is to allow sufficient storage of energy in the impactor. To do this generally requires multiple coils to allow enough elastic potential energy to be stored without leading to undue strains on any length of the wire which might lead to plastic deformation, fatigue fracturing, etc. More turns, however, give rise to a deeper spring and hence lead to a greater space requirement in the device. For many devices, two turns are adequate. The turns must be designed not to tighten on the locating peg (FIGS. 2 and 3).

The shaft region (6) of the impactor serves several functions. It allows a greater length of impactor head travel than resetting motion and allows the impactor head motion to be particularly springy, i.e. it can create a whiplash effect as stored potential energy is released during travel, and it serves as the part of the impactor against which the activator component pushes during resetting (FIG. 2) and the part which pushes the activator component out of the way during impactor flight.

The impactor cantilevered arm (8), also referred to herein as the impactor head, is the most critical region of all. The crown (10) of the cantilevered arm (8) is curved, e.g. 10 mm radius and it is aligned to strike the centerline of the medicament tape to ensure central impaction. This curvature also serves to give consistent impactions, no matter whether the tape lies at a slight angle to that intended. If the head were straight, then any small misalignments of the tape prior to an impaction would tend to give inconsistent behavior, with the impactor head sometimes striking parallel along its length, sometimes striking the tape with its top corner first, or sometimes striking the tape first with its elbow where it joins the arm region. In addition, the curvature of the head allows the tape to be bent into a three-dimensional surface as it is struck, giving rise to more complex vibrations in the tape and thus serving better to remove and aerosolise powder from it. Because only the center of the tape is initially contacted by the impactor head, the vibrations set up are less likely to be damped out by contact with the head. Furthermore, the curvature ensures that the end of the impactor wire cannot reach the tape and damage, perforate, or even break it. Finally, the curved top of the impactor steers the tape correctly to the front of the impactor head during insertion of a new cassette of tape by the patient, thereby ensuring that the tape cannot be inserted behind the impactor.

The end of the cantilevered arm (8) may be bent further, through 180°, to reduce the risk of a patient scratching their finger on it. Alternatively, the end may be dipped, to form a small spherical head for the same reason. Preferably, a tunnel should cover the impactor head to prevent the patient being able to contact the impactor in inhalation devices.

The impactor cantilevered arm (8) should be as low in mass as possible, commensurate with having sufficient strength and rigidity to strike the tape in the correct position and at the correct time. The reason for a low mass requirement is that this characteristic allows maximum transfer of energy to the medicament coated tape. Considering the impactor head as an object of mass $M_H$ and initial velocity $V_H$ ($V_{H2}$ after collision), and a drug particle as an initially stationary object of mass $M_P$ and final velocity $V_P$ after being struck by the head:

$$M_H V_N = M_H V_{H2} + M_P V_P$$

and $$M_M V_M^2 = M_M V_{H2}^2 + M_P V_P^2$$

in a two body system assuming no losses and where momentum and kinetic and kinetic energy are conserved.

If $M_H = kM_P$ then substitution leads to:

$$V_P/V_H = \frac{2k}{k+1}$$

From this equation come the following observations:

As $k \rightarrow 0$, $V_P, /V_M \rightarrow 0$ i.e. a small impactor does not move a large drug particle.

For $k=1$, $V_P/V_H=1$ i.e. Newton's cradle situation

As $k \rightarrow \infty$, $V_P V_H \rightarrow 2$ i.e. the maximum possible velocity of the drug particle is twice that of the incoming impactor (this can be viewed as the drug particle approaching at $-V_H$ and bouncing off at $+V_H$ in the impactor's frame of reference). Hence in order to impart as much velocity as possible to the drug particles (i.e. in order to transfer as much kinetic energy as possible to them), the velocity of the impactor should be as high as possible, i.e. the impactor head should have as low a mass as possible for a given kinetic energy stored in the spring region of the impactor.

For an impactor shown in FIG. 1, typical times of flight of approximately 1 ms are needed to travel ~10 mm to the tape, i.e. mean speed ~10 m/s; maximum speed just prior to impaction of the rear of the powder coated tape being in excess of this.

The impactor is stopped just after striking the tape, because follow-through could cause tearing of the tape, could pull a loop of excess tape off the supply spool, cause the tape to block the airflow channel, etc.

FIG. 2 illustrates a dry powder inhaler of the type disclosed in W090/13328, W092/08509 and GB 9123953; the full details of operation of the inhaler are disclosed in these references, the full disclosures of which are incorporated herein by reference. FIG. 2 shows the inhaler during closure of the mouthpiece cover.

The inhaler comprises a housing (20), mouthpiece (22) incorporating a deagglomerator (24) and a mouthpiece cover (26). The dry powder medicament is carried on an elongate carrier shown in dashed outline (27) which extends from a supply spool (28) to a take-up spool (30).

The inhaler comprises an impactor (32) which may have the form as shown in FIG. 1 and is positioned with the coil of the spring over locating peg (34).

The impactor (32) is engageable by an activator component (36) which forms part of a breath-actuated mechanism comprising a vane (38) which is movable in response to inspiration through the mouthpiece (22). The impactor (32) is moved to a primed position during closing of the mouthpiece cover (26) by action of reset arm (40) on activator (36). The impactor (32) is retained in the primed position by the activator component which is held by catch component (37) until the patient inspires through the mouthpiece (22) causing movement of vane (38) which results in the breath-actuation mechanism moving the catch (37) releasing the activator component (36) and the impactor (32). The impactor springs forward such that the head (cantilevered arm (8)) hits the rear of the tape in the middle of the 20 mm long impaction region of the tape, thereby releasing powder from the tape into the patient's inspiratory air flow.

The embodiment illustrated in FIG. 3 shows an inhaler (102) of the present invention, comprising a housing (104, 104a) defining air inlets (106, 108) and a slit deagglomerator (110) for outlet of the powder aerosol. A mouthpiece (140) clips onto the housing (104, 104a), defining a mouthpiece orifice (142) for insertion into the patient's mouth. Curved surfaces (112, 114) guide the powder aerosol towards slit (110). A desiccant cartridge (116) may be housed in the housing part (104, 104a). A tape supply spool, comprising a flange (not shown) and a hub (118) is mounted in the housing, together with a tape take-up spool, comprising a flange (not shown) and a hub (120). A microdimpled tape (122) coated with micronised drug powder on the side facing the mouthpiece (140) between corners (124,126) is affixed to the spool hubs (118, 120). The length between corners (124, 126) is the impacted region of the tape and in a preferred embodiment is 12 mm long. A mouthpiece part (140) clips removably onto the housing (104a), defining a mouthpiece orifice (142) through which aerosolised drug powder passes to the patient.

The inhaler releases medicament from the impacted region of the tape by striking the rear (uncoated) side of it with the head (shown at (138), coming out of the plane of the figure) of a spring steel impactor (128) which also comprises a two turn coil region (134), loosely positioned around a peg (136) in the housing (104), and a tail (130) bearing on the inside of the housing wall at (132). The impactor is generally similar to that shown in FIG. 1 but is cranked as shown in FIG. 3, the additional bend in the arm region of the impactor being provided to allow access to the rear of the tape in the shorter (12 mm) impaction region of the tape. A release component (144) is pivotally mounted on the housing (104) at pivot pin (152). The release component additionally comprises a flexible arm (146) terminating at a push button (148) at the top of the inhaler, with barbs (150) preventing the button being pulled. Mouthpiece cover (154), pivoted at (136), above the impactor coil (134), comprises a reset arm (156) with surface (158) to push the impactor (128) into a primed position. The impactor (128) in turn pushes on surface (160) of the release component (144), thereby causing it to rotate clockwise and for surface (162) to catch the elbow at the bottom of the impactor head (138) i.e., the intersection of shaft (6) and cantilevered arm (8). In the event of the release component being already in a clockwise position such that it obstructs the impactor during resetting, surface (164) is contacted by the impactor, causing the release component to rotate anti-clockwise until surface (160) is contacted to cause it to rotate clockwise.

Operation of the inhaler is as follows. First, the patient opens the mouthpiece cover (154). In the simplest embodiment of the device the patient then rotates a knob protruding from take-up spool (120), to rotate said spool anti-clockwise by one ratchet or detent position (60°). This is sufficient, with a 23 mm diameter hub, to advance 12 mm of tape, equivalent to the length between corners (124, 126). After 220 doses of 165 μm thick tape, the take-up spool will have grown to around 36 mm diameter at a typical tape winding tension. The advanced length for a 60° turn of the knob will then be nearly 19 mm, but as the drug dose is determined by the impacted region's length, not by the tape advance length if that is greater, then the drug dose will remain consistent. The supply spool (118) rotates with a fairly high level of friction, in order to ensure the advanced tape remains tight, and non-reverse means (not shown) are provided on the take-up spool (120).

In an alternative embodiment (not shown), an additional arm on the mouthpiece cover (154) pushes on one of a series of radial grooves on an extension protruding from the take-up spool (120), causing it to rotate 60° anti-clockwise upon closing of the mouthpiece cover (154). In a further embodiment (not shown) priming may be effected upon opening the cover.

The patient then places mouthpiece (140) into their mouth, and inhales, causing air to enter the inhaler at inlets (106, 108) and pass the tape to reach the deagglomerator slit (110) and mouthpiece orifice (142). Soon after the start of inhalation the patient pushes button (148), causing the release block (144) to rotate anti-clockwise slightly about pivot pin (152). The causes surface (162) to release the elbow of the impactor head (138), causing the impactor head (138) to travel towards and strike the rear of the impaction region of the tape. This releases a dose of powdered medicament which is entrained in the airstream and passes through the deagglomerator slit (110) which breaks up agglomerates of micronised drug particles to enable them to reach the patient's lungs more effectively.

The patient then closes the mouthpiece cover (154), causing the reset arm (156) to push impactor (128) back until it contacts surface (160) of the release component (144), thereby causing it to rotate clockwise again. This action stores energy in the impactor spring by straining it, tail (130) being unable to move. The impactor (128) is thus primed. The next opening of the cover (154) will then allow the impactor to move forward slightly until the elbow at the bottom of the impactor head (138) is held by surface (162) and the operation cycle thus starts to be repeated.

We claim:

1. A device for delivering a powder comprising:

a flexible sheet material carrying a powder to be delivered on a surface thereof; and an impactor for dislodging said powder from said sheet material comprising (a) a shaft having a first end that is mounted within the device, and (b) a cantilevered arm extending from said shaft to a second, free end that is moveable between a first, primed position and a second position in which at least a portion of said arm impacts a substantially planar portion of said flexible sheet material, said free end being resiliently biased toward said second position, the movement of said shaft between said first and second positions defining a plane of motion, at least a portion of said cantilevered arm, disposed intermediate (i) the intersection of said arm with said shaft and (ii) said free end, extending out of a first plane that includes said shaft and is perpendicular to said plane of motion, towards a second plane that is defined by said substantially planar portion of said flexible sheet material.

2. A device of claim 1 wherein a second portion of said cantilevered arm, between said intermediate portion and said free end, intersects said first plane, and said free end extends out of said first plane in a direction away from said second plane.

3. A device of claim 2 wherein said second portion defines an arc segment.

4. A device of claim 1 wherein said shaft and said cantilevered arm comprise a unitary resilient member.

5. A device of claim 4 wherein said unitary resilient member is formed of spring steel.

6. A device of claim 5 wherein the spring steel has a circular cross-section having a diameter of approximately 1 mm.

7. A device of claim 6 wherein said free end is biased toward said second position by a spring.

8. A device of claim 7 wherein said spring, said shaft and said cantilevered arm together comprise a single unitary resilient member.

9. A device of claim 8 wherein said spring is positioned adjacent said fixed end of said shaft.

10. A device of claim 1 wherein said cantilevered arm extends at an angle of approximately 90° with respect to said shaft.

11. A device of claim 3 wherein said arc segment has a radius of curvature of from about 10 mm to about 40 mm.

12. A device of claim 1 wherein said cantilevered arm has a length of about 14 mm.

13. A device of claim 1 further comprising a support structure shaped and positioned to support said substantially planar portion of said sheet material in a position for engagement with a portion of said arm when said arm is moved to said second position.

14. A device of claim 13 wherein said sheet material is elongate and said support structure comprises a pair of support members disposed in opposed spaced relation along the longitudinal axis of said sheet material.

15. A device of claim 1 wherein said free end is biased towards said second position to a sufficient extent so that when said free end is released from said primed position it moves toward said second position at a speed of at least 10 m/sec.

16. The device of claim 1 wherein the powder is a medicament.

17. The device of claim 1 further comprising a releasable latch mechanism for retaining said free end in said primed position until use of the device.

18. The device of claim 17 further comprising a camming member for returning said free end to said first, primed position after use of the device.

19. The device of claim 1 wherein the powder is micronized.

20. The device of claim 1 wherein said device is an inhaler.

21. The device of claim 1 wherein said device further comprises a housing having a mouthpiece shaped and positioned for delivery of the powder that is dislodged from the sheet to the mouth of a user of the device.

22. The device of claim 21 wherein said device further comprises a cover that is movable between a first position, in which it covers said mouthpiece, and a second position, in which it is clear of said mouthpiece.

23. The device of claim 22 further comprising a releasable latch mechanism for retaining said free end in said primed position until use of the device, and a camming member for returning said free end to said first, primed position after use of the device, and said camming member is actuated by movement of said cover between said first and second positions.

24. A device of claim 21 wherein said free end is moveable from said first position to said second position in response to said user inhaling through said mouthpiece.

25. A device of claim 1 wherein said free end is moveable from said first position to said second position in response to a user applying a force, other than a force due to the user inhaling through said mouthpiece, to the device.

* * * * *

UNITED STATES PATENT AND TRADEMARK OFFICE
CERTIFICATE OF CORRECTION

PATENT NO.   : 5,482,032

DATED        : January 9, 1996

INVENTOR(S)  : David K. Smith et al.

It is certified that error appears in the above-identified patent and that said Letters Patent is hereby corrected as shown below:

Column 4, line 23, in the equation, "$M_H V_N=$" should be --$M_H V_H=$--;

Column 4, line 25, in the equation, "$M_M V_M^2=M_M$" should be --$M_H V_H^2=M_H$--;

Column 4, line 38, "$V_P/V_M$" should be --$V_P/V_H$--.

Column 7, claim 7, line 27, "6" should be --1--.

Signed and Sealed this

Fourth Day of March, 1997

BRUCE LEHMAN

Attest:

*Attesting Officer*     *Commissioner of Patents and Trademarks*